United States Patent
Senet et al.

(10) Patent No.: US 6,858,751 B1
(45) Date of Patent: Feb. 22, 2005

(54) PROCESS FOR PREPARING ALIPHATIC FLUOROFOMATES

(75) Inventors: Jean-Pierre Senet, La Chapelle la Reine (FR); Gérard Sennyey, Gif sur Yvette (FR); Philippe Delabrouille, Brouy (FR); Denis Grenouillat, Athis-Mons (FR)

(73) Assignee: Isochem, Paris Cedex (FR)

( * ) Notice: Subject to any disclaimer, the term of this patent is extended or adjusted under 35 U.S.C. 154(b) by 0 days.

(21) Appl. No.: 09/937,276
(22) PCT Filed: Mar. 17, 2000
(86) PCT No.: PCT/FR00/00662
§ 371 (c)(1),
(2), (4) Date: Sep. 24, 2001
(87) PCT Pub. No.: WO00/59859
PCT Pub. Date: Oct. 12, 2000

(30) Foreign Application Priority Data

Apr. 2, 1999 (FR) .............................. 99 04125

(51) Int. Cl.$^7$ ................................ C07C 69/63
(52) U.S. Cl. ...................................... 560/227
(58) Field of Search ........................ 560/227

(56) References Cited

U.S. PATENT DOCUMENTS 3,088,975 A   5/1963 Fawcett et al.
4,612,143 A   9/1986 Piteau et al.

FOREIGN PATENT DOCUMENTS

GB   1214009   11/1970
GB   1216639   12/1970

OTHER PUBLICATIONS

"An Efficient and Convenient Synthesis of Fluoroformates and Carbamoyl Fluorides", Cuomo, et al, J. Org. Chem., vol. 44, No. 6, 1979, p. 1016.
"Alpha Fluorinated Ethers II Alkyl Fluoroalkyl Ethers", Aldrich et al., J. Org. Chem., vol. 29, No. 1, 1964, pp 11–15.
"The Chemistry of Carbonyl Fluoride. I. The Fluorination of Organic Compounds", Fawcett et al, J. Amer. Chem. Soc., vol. 84, No. 22, 1962, pp. 4275–4286.
"Useful Syntheses of Fluoroformates and 1–Alkenyl Carbonates", Vu Anh Dang, Penn. State Univ., 1986, Thesis.

*Primary Examiner*—Paul J. Killos
(74) *Attorney, Agent, or Firm*—Bucknam and Archer

(57) ABSTRACT

A method for the production of aliphatic fluoroformates, wherein carbonyl fluoride is made to react with aliphatic alcohol in the presence of sodium fluoride in ether at a temperature of −20° to 50° C. The method is carried out using carbonyl fluoride obtained by reacting phosgene with surplus powdered sodium fluoride, whereby the grains thereof have a specific surface of 0.1 m$^2$/g or more and/or an average diameter of 20 μm or less, at a temperature ranging from 25° to 120° C. The method enables unstable fluoroformates such as tertiobutyl to be obtained with excellent yields.

28 Claims, No Drawings

PROCESS FOR PREPARING ALIPHATIC FLUOROFOMATES

The present invention relates to a process for preparing aliphatic fluoroformates by reacting alcohols with carbonyl fluoride. The invention relates in particular to the preparation of fluoroformates by means of carbonyl fluoride obtained from phosgene.

Fluoroformates are known compounds, which are useful as intermediate products in particular for forming alkyl fluorides. Some are particularly useful for protecting the amino group of amino acids.

Fluoroformates can be prepared by halogen exchange, starting with the analogous chloroformates, by reacting them with potassium fluoride. However, this method cannot be used when the compounds are unstable or contain reactive carbons or functions in the molecule.

Several other processes for preparing fluoroformates have been proposed, but they are not entirely satisfactory. According to one of the oldest processes, described in French patent No. 1 549 815, the preparation of t-butyl fluoroformate is carried out by reacting carbonyl fluorochloride or fluorobromide with tert-butanol, but this process has several drawbacks. Carbonyl fluorochloride and fluorobromide are very difficult to prepare and are consequently very uncommon. The temperature at the start of the reaction should be very low, in the region of −70° C., and a complex temperature cycle from −70° C. to 0° C. should then be carried out, which results in very high operating costs. The fluoroformate obtained is impure on account of the by-products formed or the unconverted starting material.

According to another process, the reaction of the alcohol is carried out with a mixture of phosgene and of fluoro phosgenes, in the presence of isobutylene and under high pressures, as described in French patent No. 2 010 922, but in this case specific plants are required.

According to European patent No. 176,412, fluoroformates are prepared by reacting an alpha-chloro carbonate with an alkaline fluoride, but the preparation of the starting carbonate requires an additional starting material and several steps. Furthermore, the reaction of the carbonate with the fluoride produces the fluoroformate with an aldehyde which needs to be removed.

Laboratory tests for preparing fluoroformates, starting with phosgene, have been carried out. Phosgene was mixed at a temperature of −78° C. with sodium fluoride, in a solvent mainly comprising sulfolane, and the resulting products were then reacted with potassium fluoride and the alcohol, but the results obtained could not be reproduced.

There was consequently a need for a process for preparing aliphatic fluoroformates which is simple, reproducible and which makes it possible to obtain fluoroformates in good yields and with good stability. A process has now been discovered which has these characteristics.

According to the process of the invention, carbonyl fluoride is reacted with an aliphatic alcohol, in the presence of sodium fluoride, in a solvent chosen from ethers, at a temperature of between about −20° C. and about 50° C.

The term aliphatic should be understood as covering saturated or unsaturated, substituted or unsubstituted, aliphatic, cycloaliphatic and araliphatic radicals.

The process is particularly suitable for preparing tert-butyl, benzyl, adamantyl, fluorenyl-methyl, tert-amyl or allyl fluoroformate.

The fluoroformate yields obtained by means of this process are excellent. The degree of conversion can be in the region of 100%.

The amount of carbonyl fluoride used relative to the alcohol is preferably from 1.1 to 2 mol per mole of alcohol and more particularly from 1.1 to 1.5 mol per mole.

The reaction of carbonyl fluoride with the alcohol is preferably carried out in the presence of an amount in the region of the stoichiometry and better still in an excess of sodium fluoride. In particular, an amount of from 1.1 to 2 mol of sodium fluoride per mole of alcohol is used, and even more preferably greater than 1.15 mol per mole of alcohol are used.

It has moreover been found that it is preferable to use the sodium fluoride in the form of a powder whose grains have a specific surface of greater than or equal to 0.1 $m^2/g$, and/or an average diameter of less than or equal to 20 μm. Preferably, the grains have a specific surface of greater than or equal to 0.1 $m^2/g$ and even more preferably also have an average diameter of less than or equal to 20 μm.

It has also been found that it is preferable to react the carbonyl fluoride gradually with the alcohol and also to add it to the reaction medium which contains the alcohol. Contrary to what might be expected, the symmetrical carbonate, which is a by-product of the reaction, is not formed, which is surprising since at the start of the reaction there is a deficit of carbonyl fluoride relative to the alcohol.

The ethers which are used as solvent in the reaction of carbonyl fluoride with the alcohol are cyclic or acyclic and are, for example, tert-butyl methyl ether, dioxane, tetrahydrofuran, 2-methyl-tetrahydrofuran, dibenzyl ether, ethylene glycol dimethyl ether and polyethylene glycol dimethyl ethers (glymes). Dimethoxyethane and tetraethylene glycol dimethyl ether are particularly suitable.

The amount of solvent for this reaction is generally from 1 to 3 liters of solvent per kilogram of fluoroformate to be obtained.

The reaction temperature is preferably between about −5° C. and 40° C.

It is preferable to carry out the reaction with anhydrous compounds and under anhydrous conditions.

It has furthermore been found that, contrary to the indications of the prior art, it is important, in order to obtain the best results, and in particular excellent yields, for the carbonyl fluoride to be of very high purity and in particular virtually free of chloro compounds such as, in particular, phosgene and carbonyl fluorochloride (COFCl).

One subject of the present invention is consequently also the preparation of carbonyl fluoride of very high purity, which is particularly useful for reacting with aliphatic alcohols as described above.

According to this process, the carbonyl fluoride is obtained by reacting phosgene diphosgene or triphosgene, or a mixture thereof, with an excess of sodium fluoride powder whose grains have a specific surface of greater than or equal to 0.1 $m^2/g$ and/or an average diameter of less than or equal to 20 μm, in a solvent chosen from polar aprotic solvents, at a temperature of between about 25° C. and about 120° C., followed by passing the gases present into a condenser whose temperature is between about 0° C. and about −50° C.

By performing the process for preparing carbonyl fluoride under this set of conditions, the carbonyl fluoride obtained at the condenser outlet is of very high purity, contains no carbonyl fluorochloride and virtually no phosgene.

The absence of these two gases is particularly advantageous since this thus avoids the formation of chloroformates as by-products, which previously led to a reduction in the fluoroformate yields obtained. Furthermore, chloroformates are compounds that are highly unstable and the risks of violent decomposition are thus avoided.

The characteristics of the sodium fluoride powder are important for satisfactory implementation of this process. The reason for this is that it has been found that when the grains of sodium fluoride do not have the characteristics described above, the purity of the carbonyl fluoride is markedly lower and the yields of carbonyl fluoride and of fluoroformates are markedly lower.

Preferably, the grains of sodium fluoride have a specific surface of greater than 0.1 $m^2/g$ and even more preferably also have an average diameter of less than 20 $\mu$m.

The sodium fluoride powder should be in excess relative to the phosgene. Preferably, an amount of from 3 to 5 mol of sodium fluoride per mole of phosgene is used.

The solvent, which is of course inert with respect to the reagents, is chosen from solvents which are aprotic and polar, i.e. solvents whose dielectric constant is greater than 10 and preferably greater than 20. Aliphatic nitrites are suitable for use. Acetonitrile is preferably used.

The temperature of the reaction medium is preferably between about 35° C. and 80° C. The temperature of the condenser is in particular between about −20° C. and −40° C.

The phosgene and/or its precursors are preferably introduced gradually into the reaction medium. Phosgene is generally used in gaseous form. It can also be introduced in the form of a solution in the solvent.

Diphosgene or triphosgene are generally introduced in liquid phase, optionally in solution in the solvent, in amounts that are sufficient to give the desired amount of phosgene.

The reaction is preferably carried out with anhydrous compounds and under anhydrous conditions.

The carbonyl fluoride obtained At the condenser outlet contains no carbonyl fluorochloride. It contains infinitesimal amounts of phosgene. Its purity, determined by gas chromatography, is usually greater than 99% and its yield is generally greater than 95%.

This carbonyl fluoride can be used directly to prepare fluoroformates and is preferably reacted progressively as it forms. The reaction of phosgene with sodium fluoride is then carried out in a first reactor, at a temperature preferably between about 35° C. and 80° C. An at least stoichiometric amount of phosgene is used relative to the alcohol which it is desired to convert, and preferably from 1.1 to 2 mol of phosgene per mole of the alcohol.

The amount of sodium fluoride which is reacted with phosgene is, in this case, preferably from 3 to 6 mol per mole of the alcohol to be converted and the amount of solvent for this first reaction is generally from 0.3 to 0.6 liter per mole of the alcohol.

The gases which are evolved from the reaction medium pass through the condenser and are introduced progressively into the solution of the alcohol contained in the second reactor.

The temperature of the condenser is preferably between about −20° C. and −40° C. The liquids condensed by the condenser are generally recycled into the first reactor.

The sodium fluoride used in the second reactor is preferably a sodium fluoride which has the same characteristics as that used in the first reactor.

This preferred method for preparing fluoroformates has great advantages. The manipulations are reduced. The process is simpler and more cost-effective. The yields are excellent and close to 100%.

The process using phosgene generally lasts a few hours. When the reaction is complete, the fluoroformate solution is separated from the reaction medium, generally by filtration.

In order to obtain even purer fluoroformate, it can be treated with an alkaline fluoride, preferably with sodium fluoride which in particular has the same particle size characteristics as described above. This treatment is generally carried out with the fluoroformate in solution. The purification can also be perfected by carrying out distillation.

A means has also been found for obtaining very pure fluoroformates which are solid at room temperature, generally about 20° C., in crystalline form. To do this, a compound which does not dissolve the fluoroformate, chosen from aprotic apolar solvents, in particular with a dielectric constant of less than 10, and preferably chosen from alkanes such as pentane, hexane and heptane and in particular Isopar G or Essence G, is added to the fluoroformate solution and the solution is then cooled in order to make the fluoroformate precipitate. Its purity, determined by analyses, is then generally greater than 99%.

It may be advantageous to conserve the fluoroformates, which are generally unstable, in solution. It has been discovered that the stability of fluoroformates in solution is considerably improved when about 1 to 3% by weight of dimethylformamide relative to the fluoroformate is added to the solution which it is desired to conserve. This solution can thus be conserved for several months.

The fluoroformate in solution can be used directly to carry out other reactions such as, for example, the reaction with amino acids.

The process is illustrated by the examples which follow.

Except where otherwise mentioned, in these examples, the reactions for preparing the fluoroformates and the carbonyl fluoride are carried out with anhydrous compounds and apparatus and under anhydrous conditions.

EXAMPLE 1

Preparation of Tert-butyl Fluoroformate with Preparation of Carbonyl Fluoride 189 g (4.5 mol) of sodium fluoride powder whose grains have an average diameter of 8.6 $\mu$m and a specific surface of 0.27 $m^2/g$ and 340 ml of acetonitrile are, placed in a first reactor. Mounted on this first reactor is a condenser maintained at −30° C., which is connected to a second reactor in which are placed 74 g (1 mol) of tert-butanol and 49 g (1.17 mol) of sodium fluoride of the same characteristics as above and 150 ml of tetraglyme (tetraethylene glycol dimethyl ether), and the two reactors are equipped with a stirring system. The first reactor is heated to a temperature of 50° C. and the second reactor is maintained at a temperature of about +5° C. 148.5 g (1.5 mol) of gaseous phosgene are introduced gradually into the solvent medium over about 4 hours. The gases leaving the condenser are analysed by gas chromatography and mass spectroscopy. No trace of carbonyl fluorochloride is found and only traces of less than 0.1% by mass of phosgene are found. The purity of the carbonyl fluoride is greater than 99%. The yield determined by analysis of the remaining salts is 98%.

When the production of the tert-butyl fluoroformate is complete, the gases are removed by a stream of nitrogen. The contents of the second reactor are filtered and the cake is rinsed with a few milliliters of tetraglyme.

By $^1$H NMR analysis, it is found that the conversion into tert-butyl fluoroformate is 100%.

EXAMPLE 2

Preparation of Tert-butyl Fluoroformate

For this example, the purest carbonyl fluoride sold in steel bottles and under pressure by the company Union Carbide is used.

This bottle is connected to a reactor of the same type as the second reactor in the above example, which contains the same amounts of compounds with the same characteristics, and the process is performed under the same conditions. 1 mol of carbonyl fluoride is gradually introduced.

It is found that the conversion (determined by $^1$H NMR analysis) into tert-butyl fluoroformate is thus 93%.

EXAMPLE 3

Preparation of Tert-butyl Fluoroformate 30 g (0.7 mol) of sodium fluoride whose grains have an average diameter of 15 μm and a specific surface of 0.2 m$^2$/g and 76 ml of acetonitrile are placed in a first reactor, and 11.1 g (0.15 mol) of tert-butanol, 11 g (0.26 mol) of sodium fluoride having the same characteristics as that in the first reactor and 25 ml of monoglyme (dimethoxyethane) are placed in a second reactor. The two reactors are connected as previously by means of a condenser at −30° C. The first reactor is heated to a temperature of from 55° C. to 60° C. and the second reactor is maintained at a temperature of from 20° C. to 25° C. 18.5 g (0.19 mol) of phosgene gas are introduced into the reaction medium over three hours. When the reaction is complete, a stream of nitrogen is passed through. The reaction mixture obtained from the second reactor is filtered through a prelayer of sodium fluoride having the same characteristics. The cake is rinsed with a few milliliters of monoglyme. tert-Butyl fluoroformate in solution in the monoglyme is thus collected. The amount of this fluoroformate obtained, determined by gas chromatography analysis, is 18 g, i.e. a yield of 100%. 0.36 g of dimethylformamide is added to this solution. The solution can be conserved for 6 months at a temperature of between 0° C. and 5° C.

EXAMPLE 4

Preparation of Tert-butyl Fluoroformate 75.6 g (1.8 mol) of sodium fluoride whose grains have an average diameter of 12 μm and a specific surface of 0.23 m$^2$/g and 100 ml of acetonitrile are placed in the first reactor. 22.2 g (0.3 mol) of tert-butanol, 14.7 g (0.35 mol) of sodium fluoride identical to that in the first reactor and 40 ml of tetraglyme are placed in the second reactor. The first reactor is heated to 80° C., the condenser is maintained at a temperature of −30° C. and the second reactor is maintained at a temperature of 5° C. 44.6 g (0.15 mol) of triphosgene in 100 ml of acetonitrile are introduced into the first reactor in less than one hour. The mixture is left to react for two hours and the fluoroformate formed is assayed by $^1$H NMR. The conversion into tert-butyl fluoroformate is 100%.

In another test, the triphosgene was replaced with an equivalent amount of diphosgene. The results obtained are identical.

EXAMPLE 5

Preparation of Benzyl Fluoroformate

The process is performed as in Example 1 with, in the first reactor, 168 g (4 mol) of sodium fluoride powder having the same characteristics as described in Example 1 and 320 ml of acetonitrile and, in the second reactor, 108 g (1 mol) of benzyl alcohol, 50.5 g (1.2 mol) of sodium fluoride of the same characteristics as above and 150 g of dimethoxyethane.

After introduction of 120 g of phosgene, degassing and filtration of the suspension contained in the second reactor, the solvent is removed by evaporation under reduced pressure and a fractional distillation is then carried out. 137 g of benzyl fluoroformate are thus collected (89% yield) as a colourless liquid, the characteristics of which are as follows:

Boiling point: 64° C./4 mmHg, $^1$H NMR (CCl$_4$) δ: 7.42 (s, 5H), 5.25 (s, 2H).

EXAMPLE 6

Preparation of 1-adamantyl Fluoroformate

The process is performed as in the preceding example, the sodium fluoride used being identical, but with 84 g (2 mol) of sodium fluoride and 170 g of acetonitrile in the first reactor and 76 g (0.5 mol) of 1-adamantanol, 25 g (0.6 mol) of sodium fluoride and 100 g of dimethoxyethane in the second reactor.

After introduction of 62 g of phosgene, degassing and filtration of the suspension contained in 40 the second reactor, the solvent is removed by evaporation at 45° C. under 0.1 mmHg. 90 g (91% yield) of 1-adamantyl fluoroformate are thus collected as a solid product having the following characteristics:

Melting point: 32–33° C.,

IR spectrum: 1830 cm$^{-1}$.

EXAMPLE 7

Preparation of 9-fluorenylmethyl Fluoroformate (Fmoc-F)

The process is performed as in Example 1, but with sodium fluoride whose grains have an average diameter of 9.5 μm and a specific surface of 0.25 m$^2$/g.

The first reactor contains 160 g (3.8 mol) of sodium fluoride and 310 ml of acetonitrile and the second reactor contains 196 g (1 mol) of 99.5% (HPLC) 9-fluorenylmethanol, 50 g (1.19 mol) of sodium fluoride and 340 g of dimethoxyethane. After introduction of 120 g of phosgene into the first reactor, degassing and filtration of the contents of the second reactor, about 570 g of a clear solution of light brown colour are collected. The conversion into Fmoc-F (determined by $^1$H NMR analysis) is 100%.

200 ml of Isopar G heated to 50° C. are added to 200 g of the above solution, also heated to 50° C., and the resulting mixture is concentrated to 220 ml while keeping the temperature above 30° C. throughout. This mixture is then filtered through Celite at a temperature still above 30° C. and the cake is rinsed with 50 ml of essence G at a temperature above 30° C. The filtrate is then cooled slowly to 0° C. and the crystals obtained are filtered off and rinsed twice with essence G at 0° C. (100 ml and 50 ml). After drying at 20–30° C., 58.5 g (69% overall yield) of a white crystalline product with a melting point of 41° C. and an Fmoc-F titre of greater than 99% (determined by HPLC analysis) are obtained.

EXAMPLE 8

Preparation of Tert-butyl Fluoroformate

The process is performed as in Example 1, but using a sodium fluoride powder whose grains have a specific surface of 0.19 m$^2$/g and an average diameter of 32 μm.

The conversion (determined by $^1$H NMR analysis) into tert-butyl fluoroformate is 67%.

COMPARATIVE EXAMPLE

Preparation of Tert-butyl Fluoroformate

The process is performed as in Example 1, but using a sodium fluoride powder whose grains have a specific surface of 0.09 m$^2$/g.

The conversion (determined by $^1$H NMR analysis) into tert-butyl fluoroformate is only 40%.

What is claimed is:

1. Process for preparing an aliphatic fluoroformate from an aliphatic alcohol, wherein carbonyl fluoride is reacted with the aliphatic alcohol, in a solvent chosen from ethers, at a temperature of between −20° C. and 50° C., in the presence of sodium fluoride which is in the form of a powder whose grains have a specific surface of greater than or equal to 0.1 m$^2$/g.

2. Process according to claim 1, wherein the grains of sodium fluoride have an average diameter of less than or equal to 20 μm.

3. Process according to claim 1, wherein the carbonyl fluoride is introduced gradually into the reaction medium which contains the alcohol.

4. Process according to claim 1, wherein the amount of carbonyl fluoride used is from 1.1 to 2 mol per mole of alcohol.

5. Process according to claim 1, wherein the carbonyl fluoride is obtained by reacting phosgene, diphosgene, triphosgene, or a mixture thereof, with an excess of sodium fluoride powder whose grains have a specific surface of greater than or equal to 0.1 m$^2$/g and/or an average diameter of less than or equal to 20 μm, in a solvent chosen from polar aprotic solvents, at a temperature of between 25° C. and 120° C., and after passage of the gases present into a condenser whose temperature is between 0° C. and −50° C.

6. Process according to claim 1, wherein the amount of sodium fluoride used during the reaction of the alcohol with carbonyl fluoride is between 1.1 and 2 mol per mole of the alcohol.

7. Process according to claim 1, wherein for the reaction of the alcohol with carbonyl fluoride, the solvent is chosen from tert-butyl methyl ether, dioxane, tetrahydrofuran, 2-methyletrahydrofuran, dibenzyl ether, ethylene glycol dimethyl ether and polyethylene glycol dimethyl ethers.

8. Process according to claim 1, wherein the fluoroformate obtained is purified by treating it with an alkaline fluoride.

9. Process according to claim 1, wherein 1 to 3% by weight of dimethylformamide is added to the fluoroformate solution.

10. Process according to claim 4, wherein when it is a solid, the fluoroformate is obtained in crystalline form by adding to the fluoroformate solution a compound which does not dissolve the fluoroformate, chosen from apolar aprotic solvents, after which the fluoroformate is made to precipitate.

11. Process for preparing carbonyl fluoride, wherein phosgene, diphosgene or triphosgene, or a mixture thereof, is reacted with an excess of sodium fluoride powder whose grains have a specific surface of greater than or equal to 0.1 m$^2$/g and/or an average diameter of less than or equal to 20 μm, in a solvent chosen from polar aprotic solvents, at a temperature of between 25° C. and 120° C., and the gases present are then passed into a condenser whose temperature is between 0° C. and −50° C.

12. Process according to claim 11, wherein the grains of sodium fluoride have a specific surface of greater than or equal to 0.1 m$^2$/g.

13. Process according to claim 11, wherein the grains of sodium fluoride have an average diameter of less than or equal to 20 μm.

14. Process according to claim 11, wherein the amount of sodium fluoride reacted with the phosgene is from 3 to 5 mol per mole of phosgene.

15. Process according to claim 11, wherein the phosgene and/or its precursors are introduced gradually.

16. Process according to claim 11, wherein the solvent is acetonitrile.

17. Process according to claim 11, wherein it is performed with anhydrous compounds and under anhydrous conditions.

18. Process according to claim 11, wherein liquids condensed by the condenser are recycled into the reaction medium.

19. Process according to claim 11, wherein phosgene is reacted with sodium fluoride.

20. Process according to claim 1, wherein the aliphatic alcohol is chosen from the group comprising tert-butanol, benzyl alcohol, adamantanol, fluorenyl-methanol, tert-amyl alcohol and allyl alcohol.

21. Process according to claim 5, wherein the grains of sodium fluoride have a specific surface of greater than or equal to 0.1 m$^2$/g.

22. Process according to claim 5, wherein the grains of sodium fluoride have an average diameter of less than or equal to 20 μm.

23. Process according to claim 5, wherein the amount of sodium fluoride reacted with the phosgene is from 3 to 5 mol per mole of phosgene.

24. Process according to claim 5, wherein the phosgene and/or its precursors are introduced gradually.

25. Process according to claim 5, wherein the solvent is acetonitrile.

26. Process according to claim 5, wherein it is performed with anhydrous compounds and under anhydrous conditions.

27. Process according to claim 5, wherein the liquids condensed by the condenser are recycled into the reaction medium.

28. A process for the preparation of an aliphatic fluoroformate by the reaction of carbonyl fluoride with an aliphatic alcohol wherein the carbonyl fluoride is obtained by reacting phosgene, diphosgene or triphosgene, or a mixture thereof, with an excess of sodium fluoride powder whose grains have a specific surface of greater than or equal to 0.1 m$^2$/g and/or an average diameter of less than or equal to 20 μm, in a solvent chosen from polar aprotic solvents, at a temperature of between 25° C. and 120° C., and the gases present are then passed into a condenser whose temperature is between 0° C. and −50° C.

* * * * *